(12) United States Patent
Plotnikov et al.

(10) Patent No.: US 6,869,214 B2
(45) Date of Patent: *Mar. 22, 2005

(54) PRESSURE PERTURBATION CALORIMETRY INSTRUMENTS AND METHODS

(75) Inventors: Valerian V. Plotnikov, Sunderland, MA (US); John F. Brandts, Leeds, MA (US); J. Michael Brandts, Holyoke, MA (US)

(73) Assignee: MicroCal LLC, Northampton, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/354,934

(22) Filed: Jan. 30, 2003

(65) Prior Publication Data

US 2004/0024542 A1 Feb. 5, 2004

Related U.S. Application Data

(62) Division of application No. 09/961,872, filed on Sep. 24, 2001, now Pat. No. 6,513,969, which is a division of application No. 09/858,622, filed on May 16, 2001, now Pat. No. 6,485,173, which is a division of application No. 09/362,412, filed on Jul. 28, 1999, now abandoned.

(51) Int. Cl.[7] .................. G01K 17/00; G01N 25/00
(52) U.S. Cl. .................. 374/31; 374/10; 374/33; 374/11
(58) Field of Search ............... 374/10, 11, 12, 374/31, 34; 73/708, 729, 730; 702/130; 700/299, 300

(56) References Cited

U.S. PATENT DOCUMENTS

| 3,088,319 | A | 5/1963 | Neumayer ................ 374/54 |
|---|---|---|---|
| 3,665,761 | A | 5/1972 | Gregory ................... 374/31 |
| 3,875,788 | A | 4/1975 | Mills ...................... 374/10 |
| 4,055,982 | A | 11/1977 | Ter-Minassian et al. |
| 4,255,961 | A | 3/1981 | Biltonen et al. ............ 374/11 |
| 4,812,051 | A | 3/1989 | Paulik et al. |
| 4,892,707 | A | 1/1990 | Stockton et al. ............ 374/31 |
| 5,211,477 | A | 5/1993 | Li |
| 5,224,775 | A | 7/1993 | Reading et al. |
| 5,226,292 | A | 7/1993 | Urry |
| 5,288,149 | A | 2/1994 | Meyer |
| 5,295,745 | A | 3/1994 | Cassettari et al. .......... 374/10 |
| 5,813,763 | A | 9/1998 | Plotnikov et al. .......... 374/11 |
| 5,876,118 | A | 3/1999 | Vogel |

FOREIGN PATENT DOCUMENTS

JP     0326948 A   * 11/1991   .......... G01N/25/16

OTHER PUBLICATIONS

DiLorenzo, et al., "Heat Capacity of Solid State Biopolymers by Thermal Analysis", 1999, Journal of Polymer Science Part B: Polymer Physics, vol. 37, No. 37, pp. 2093–2102.*

(List continued on next page.)

Primary Examiner—Christopher W. Fulton
Assistant Examiner—Mirellys Jagan
(74) Attorney, Agent, or Firm—Wilmer Cutler Pickering Hale and Dorr LLP

(57) ABSTRACT

A calorimeter that includes a sample cell, a reference cell, a pressure system that applies a variable pressure to the sample cell, and a pressure controller that controls the pressure applied by the pressure system to the sample cell. By applying identical pressure perturbations to both the sample and reference cells over a range of temperatures, the calorimeter can be used to accurately calculate both the thermal coefficient of expansion of various substances, and the volume change of molecules undergoing a structural transition.

12 Claims, 6 Drawing Sheets

OTHER PUBLICATIONS

Knapp, et al., "Thermal Unfolding of Small Proteins with Sh3 Domain Folding Pattern", 1998, Proteins: Structure, Function, and Genetics, vol. 31, No. 3, pp. 309–319.*

Palma, et al., "Computational studies on mutant protein stability: The correlation between surface thermal expansion and protein stability", 1999, Protein Science, vol. 8, pp. 913–920.*

Randzio, et al., "An automated calorimeter for the measurement of isobaric expansivities and of isothermal compressibilities of liquids by scanning pressure from 0.1 to 400 Mpa at temperatures between 303 and 503K", J. of Chem. Thermodynamics, vol. 20, pp. 937–948, 1988.*

* cited by examiner

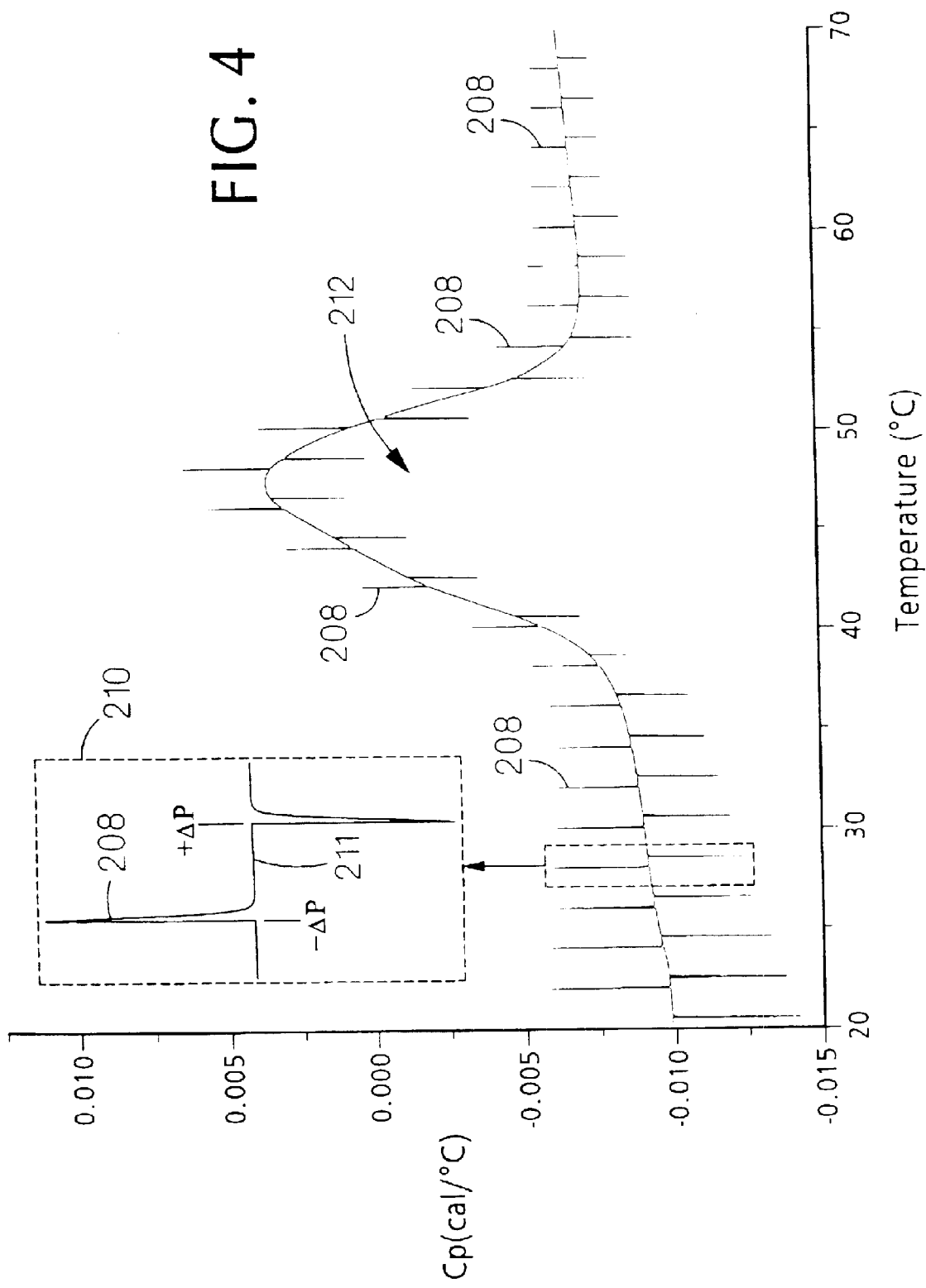

PRESSURE PERTURBATION CALORIMETRY INSTRUMENTS AND METHODS

CROSS-REFERENCE TO RELATED APPLICATIONS

This application is a division of application Ser. No. 09/961,872, filed on Sep. 24, 2001, (now U.S. Pat. No. 6,513,969), which is a division of application Ser. No. 09/858,622, filed on May 16, 2001, (now U.S. Pat. No. 6,485,173), which is a division of application Ser. No. 09/362,412, filed on Jul. 28, 1999, abandoned, the contents of each of which are incorporated herein by reference.

BACKGROUND OF THE INVENTION

The invention relates to calorimeters, e.g., microcalorimeters, and calorimetry methods.

Microcalorimeters are devices that measure very small quantities of heat. In chemistry, biochemistry, cell biology, and pharmacology, ultrasensitive microcalorimeters are frequently used to measure thermodynamic properties of biological macromolecules, such as proteins.

A typical microcalorimeter has two cells, a "reference cell" filled with a liquid, and a "sample cell" filled with a dilute solution of a test substance, e.g., a macromolecule, in the same liquid. By comparing the heat evolved or absorbed by the two cells in response to changes in certain stimuli, such as temperature or concentration of a ligand, information about the test substance can be determined.

There are generally two popular types of microcalorimeters: the differential scanning calorimeter and the isothermal titration calorimeter. The differential scanning calorimeter automatically raises or lowers the temperature of the system at a given rate, while monitoring any temperature differential that arises between the two cells. From the temperature differential information, small differences between the amount of heat absorbed or released by the sample cell in comparison to the reference cell can be determined and attributed to the test substance.

In isothermal titration calorimetry, the instrument maintains a constant temperature while the concentration of an additional substance added to the cells is varied. The additional substance can be, e.g., a ligand that binds to the test substance in the sample cell. The instrument measures the heat absorbed or released as the newly introduced ligand binds to the test substance. By repeating the titration experiment using multiple additions of the ligand until binding is complete, various information concerning the interaction between the test substance and the ligand, e.g., stoichiometry, binding constant, and heat of binding, can be determined.

SUMMARY OF THE INVENTION

In general, in one aspect, the invention features a calorimeter that includes a sample cell, a reference cell, a pressure system that applies a variable pressure to the sample cell, and a pressure controller that controls the pressure applied by the pressure system to the sample cell.

Embodiments of this aspect of the invention may include one or more of the following features. The pressure system can apply the variable pressure to both the sample cell and the reference cell simultaneously. For example, the pressure system can be a pressure chamber that communicates continuously with both the sample cell and the reference cell. The pressure controller can include first and second pressure sources that apply first and second pressures, respectively, to the pressure chamber, and a control valve can be used to regulate whether the first or second pressure is applied to the chamber.

The calorimeter can further include a heat monitoring system that determines differences between the amount of heat absorbed or released by the sample cell and by the reference cell. The heat monitoring system can include a temperature sensor that monitors a temperature differential between the two cells that arises, e.g., in response to a change in the pressure applied by the pressure system.

The sample cell can be a vessel shaped to contain a liquid, and the pressure system can apply the variable pressure to a liquid holding portion of the sample cell. The reference cell can be substantially identical in mass and volume to the sample cell.

The reference cell can contain a liquid, and the sample cell can contain a solution that includes the liquid and a test substance, such as a biopolymer.

The calorimeter can also have an electrical control system electrically coupled to the pressure controller. The electrical control system includes, for example, a computer program that causes the pressure controller to periodically vary the pressure applied by the pressure system. In addition, the calorimeter can include a heating assembly thermally coupled to the sample and reference cells and electrically coupled to the control system. The same computer program can also cause the heating assembly to change the temperature of the sample and reference cells at a rate specified by a user, and can cause the pressure controller to periodically vary the pressure applied by the pressure system.

The calorimeter can also have a temperature sensor, that monitors a temperature differential between the sample and reference cells. The computer program stores in memory information sufficient to determine temperature differentials between the sample and reference cells that arise in response to each change in the pressure applied by the pressure system. For example, the program can store either the actual temperature differentials between the cells or the differential power applied to the sample cell versus the reference cell in order to maintain the sample and reference cells at substantially equal temperatures.

In another aspect, the invention features a calorimeter that includes a sample cell, a reference cell, a pressure system in continuous communication with both the sample cell and the reference cell, and a pressure controller that controls pressure applied by the pressure system. The pressure system is configured to apply a pressure to both cells, and the pressure controller is configured to vary the pressure applied by the pressure system.

Embodiments of this aspect of the invention can further include, e.g., a heat monitoring system that determines the differential heat effect between the sample and reference cells in response to a change in the pressure applied by the pressure system.

In another aspect, the invention features a computer program, disposed on a computer-readable medium, for automating operation of a microcalorimeter that includes features of the calorimeters described above. The computer program includes instructions for causing a processor to periodically vary a pressure applied to the sample and reference cells, and store in memory information sufficient to determine temperature differentials that result when the pressure is varied. The computer program can also cause the heating assembly to scan the temperature of the sample and reference cells at a rate specified by a user.

In another aspect, the invention features a method of performing calorimetry. The method includes: (1) providing a calorimeter that has a reference cell and a sample cell, where the reference cell contains a liquid, and the sample cell contains a solution that includes the liquid and a test substance; (2) varying the pressure above the liquid in the sample cell and the solution in the reference cell; and (3) determining a differential heat effect between the sample cell and the reference cell in response to a change in the pressure applied by the pressure system.

Embodiments of this aspect of the invention may include one or more of the following features. The varying step can include applying a pressure perturbation to both the sample cell and the reference cell. The determining step can include measuring a difference between the temperature of the sample cell and the temperature of the reference cell.

In another aspect, the invention features a method of determining a thermal coefficient of expansion of a substance. The method includes: (1) providing a first liquid holder containing the substance, and a second liquid holder containing a solution in which the substance is not present; (2) applying a pressure perturbation to the solutions in the first and second liquid holders at a known temperature; (3) determining a differential heat effect between the first and second liquid holders in response to the pressure perturbation; (4) calculating, from the differential heat effect, the heat effect of the substance in response to the pressure perturbation; and (5) using the first and second laws of thermodynamics to determine the thermal coefficient of expansion of the substance at the known temperature. The applying step through the using step can then be repeated at a plurality of known temperatures, allowing construction of a function for the thermal coefficient of expansion of the substance as a function of temperature.

In another aspect, the invention features a method of determining the change in volume occupied by a target molecule (e.g., a protein, an oligonucleotide, a lipid, or a carbohydrate) as the molecule transitions from a first structure to a second structure in response to a change in temperature. The method includes: (1) providing a first liquid holder containing a plurality of the target molecules, and a second liquid holder containing no target molecules; (2) applying a pressure perturbation to the contents of the first and second liquid holders at a plurality of different temperatures, where the plurality of temperatures includes temperatures at which the molecules are transitioning from the first structure to the second structure; (3) determining a differential heat effect between the first and second liquid holders in response to each pressure perturbation; (4) calculating, from each differential heat effect, the heat effect of the molecule in response to each pressure perturbation; and (5) calculating the change in volume occupied by the molecule from a data set that includes the pressure perturbation values, the temperatures at which each pressure perturbation was applied, the volume of an individual target molecule in either its first or its second structure, and the heat effect of the molecule for each pressure perturbation.

The second calculating step can include: (a) determining the thermal coefficient of expansion, $\alpha$, of the molecule at each temperature T in the data set; (b) constructing a function $\alpha(T)$ from the data set; (c) identifying, from the data set, a transition temperature range during which the molecule is actively transitioning from the first structure to the second structure; (d) constructing a second function $\alpha_2(T)$ for the transition range, where $\alpha_2(T)$ represents the thermal expansion coefficients that would have been measured in the transition range if the molecule did not change volume as it transitioned from its first to its second structure; (e) calculating the total area between $\alpha(T)$ and $\alpha_2(T)$ over the transition range; and (f) multiplying the total difference by the molar volume of the molecule.

Embodiments of the invention may include one or more of the following advantages. The new calorimeters allow a user to vary more than one intensive variable, e.g., temperature and pressure, or concentration and pressure, while conducting an experiment. The additional data gathered by applying pressure perturbations while varying temperature or concentration allows calculation of, e.g., the thermal coefficient of expansion of a test substance, and the change in volume occupied by a test substance as it changes structure in solution.

Operation of the new calorimeters can be automated by new software.

BRIEF DESCRIPTION OF THE DRAWINGS

FIG. 4 is a graph displaying sample data gathered using the calorimeter of FIG. 1.

DESCRIPTION OF THE PREFERRED EMBODIMENTS

Because existing calorimetry systems can only collect data in response to changes in one intensive variable (i.e., temperature or concentration), the information existing systems obtain on the test sample is limited. By contrast, the pressure perturbation calorimeter described below obtains data resulting from variations in either of two intensive variables: temperature and pressure. Other embodiments could utilize the two intensive variables concentration and pressure.

In brief, the instrument applies small pressure perturbations to solutions in both a reference cell and a sample cell at different temperatures, and compares the heat absorbed or released by the two cells in response to each pressure perturbation. From these measurements, certain thermodynamic properties of the test substance in the sample cell can be calculated. For example, as discussed below, the new pressure perturbation calorimetry methods are particularly useful for determining the thermal coefficient of expansion of a macromolecule, and for determining the macromolecule's volume change as it unfolds. These parameters cannot be measured with sufficient accuracy using existing technology.

Instrument Design

Figure 1:
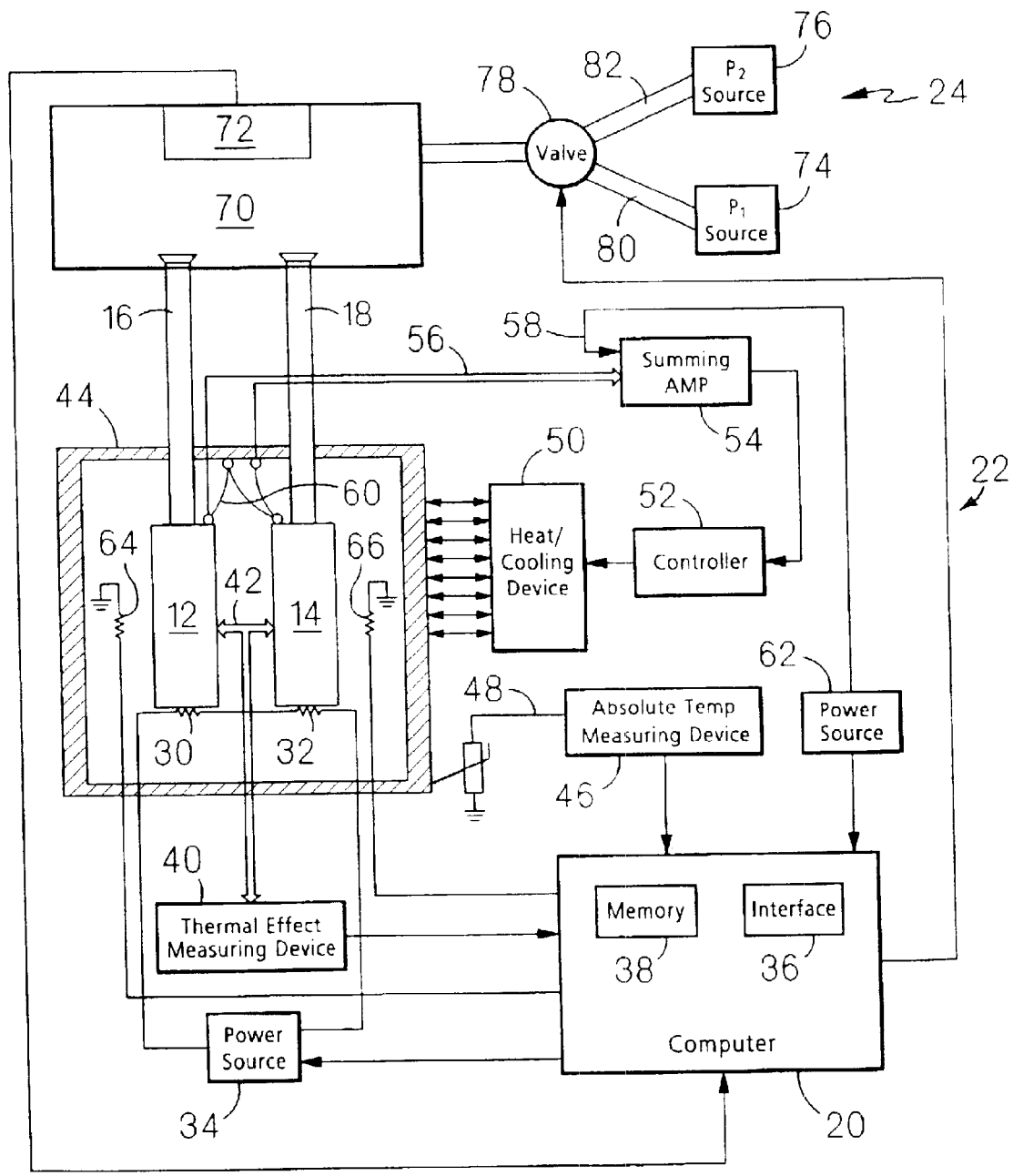
FIG. 1 is a schematic diagram of a pressure perturbation calorimeter.

FIG. 1 schematically illustrates an embodiment of a pressure perturbation calorimeter 10. Calorimeter 10 includes a reference cell 12, a sample cell 14, inlet capillary tubes 16 and 18, a computer 20, a heating assembly 22, and a pressure perturbation assembly 24. Reference cell 12 and inlet tube 16 are filled completely with a liquid solution, and sample cell 14 and inlet tube 18 are filled completely with a test substance dissolved within the same liquid of cell 12. Heating assembly 22, pressure perturbation assembly 24, and the automated method of operation will be described separately below.

The Heating Assembly and Temperature Control Modes

Heating assembly 22 is similar in design and operation to the device described in Plotnikov et al., U.S. Pat. No. 5,813,763, which is incorporated herein by reference. Heating assembly 22 raises or lowers the temperatures of cells 12 and 14 at a steady rate, or "scan rate" specified by the user. At specified points during a scan, heating assembly 22 detects any temperature differential between cells 12 and 14, and stores the information in computer memory. Assembly 22 includes multiple, separate heating elements and feedback elements, allowing the temperature of cells 12 and 14 to be regulated using several different temperature control modes.

Referring to FIG. 1, heating assembly 22 includes heating elements 30 and 32, coupled to cells 12 and 14, respectively. Heating elements 30 and 32 are driven by a power source 34 which is controlled by computer 20. Computer 20 includes an interface 36 that allows the user to input specifications, and a memory 38 for storage. Memory 38 can be, e.g., a hard drive or random access memory. Heating elements 30 and 32 are matched and are driven simultaneously by power source 34, so that cells 12 and 14 are heated at an identical rate controlled by computer 20. The rate at which the temperature of cells 30 and 32 changes is the scan rate, and is specified by the user through interface 36.

A thermal sensor 42 is coupled to cells 12 and 14 and electrically connected to a thermal effect measuring device 40. Sensor 42 continuously sends an analog signal to measuring device 40. From this signal, device 40 continuously measures the difference in temperature between cells 12 and 14, and sends the temperature differential data to computer 20 as a continuous data stream.

Computer 20 filters the temperature differential data stream into discrete data points by averaging data over discrete time intervals, and stores the discrete points in memory 38. The discrete time interval over which the data stream is averaged, the "filter time," is selected by the user in advance of a scan. For example, if the selected filter time is five seconds, computer 20 averages temperature differential data over five second intervals, and saves a single temperature differential data point for each interval.

Cells 12 and 14 are surrounded by a thermal shield 44. The temperature of thermal shield 44 is continuously monitored by an absolute temperature measuring device 46 which is activated by a sensor 48 (typically a platinum resistance thermometer device or RTD). Sensor 48 is mounted on thermal shield 44.

Thermal shield 44 is connected to a heating and cooling device 50 (e.g., an array of Peltier devices) operated by a controller 52. The signal to controller 52 comes from the output of a summing amplifier 54. Summing amplifier 54 receives two inputs, first input 56 and second input 58. First input 56 receives its signal from a sensor 60 that monitors the difference between the temperature of thermal shield 44 and the average temperature of the two cells 12 and 14. The second input 58 receives its signal from a second power source 62 whose output is controlled by computer 20. The output from absolute temperature measuring device 46 is sent to computer 20 and used to determine the appropriate signal to send to second power source 62 and subsequently to summing amplifier 54. The absolute temperature information is filtered by computer 20 and stored as discrete data points in the manner described above. The filter time intervals for the absolute temperature information are identical to the filter time intervals for the temperature differential data. The operating range for calorimeter 10 is, e.g., about −20° C. to 150° C.

Additional cell heaters 64 and 66 are located on reference cell 12 and sample cell 14, respectively. The power to heaters 64 and 66 is independently controlled directly by the output of computer 20. Cell heaters 64 and 66 generate only small amounts of heat, and are used to actively reduce any temperature differential between cells 12 and 14.

Through computer interface 36, the user can select between passive compensation, in which additional heaters 64 and 66 are not used, or various levels (typically low, medium, and high) of active compensation, in which heaters 64 and 66 are used by computer 20 to actively minimize the temperature differential between cells 12 and 14. The choice of passive compensation or various levels of active compensation is equivalent to selecting instrument response times, with most active compensation resulting in fastest response time.

Heating assembly 22 can operate in one of three modes: adiabatic, improved adiabatic, and non-adiabatic. The user selects a particular mode of operation through computer interface 36.

In adiabatic mode, second input 58 to the summing amplifier 54 is deactivated. As described previously, first input 56 relays the difference between the temperature of thermal shield 44 and the average temperature of cells 12 and 14. Based only on the temperature differential signal, summing amplifier 54 sends a signal to controller 52. In turn, controller 52 regulates heating and cooling device 50 for thermal shield 44 in relation to the signal from summing amplifier 54, thereby minimizing the temperature difference between shield 44 and the cells 12 and 14. In this way, the temperature of thermal shield 44 follows the temperature of cells 12 and 14, which is controlled by computer 20 via power source 34 and cell heaters 30 and 32.

In improved adiabatic mode, both inputs to summing amplifier 54 are activated. The signal from second input 58 represents a correction factor generated by an empirically-derived equation stored in computer memory 38. The purpose and derivation of the correction factor is described in Plotnikov, supra. The correction factor compensates for factors that limit adiabatic performance, such as heat exchange between shield 44 and the surroundings and temperature gradients within calorimeter 10.

In non-adiabatic mode, cell heaters 30 and 32 are deactivated. In this case, the temperature of cells 12 and 14 follow the temperature of thermal shield 44 by heat conduction. Since the heat conduction process is relatively slow, the temperature of the cells typically lags behind the temperature of thermal shield 44, in contrast to the former two cases where the temperature of thermal shield 44 is actively driven to follow the temperature of the cells.

The Pressure Perturbation Chamber

Pressure perturbation assembly 24 includes a pressure chamber 70, a pressure sensor 72, a first pressure source 74, a second pressure source 76, and a two-position control valve 78. Pressure chamber 70 communicates directly and continuously with both the liquid in tube 16 and reference cell 12, and the test substance solution in tube 18 and reference cell 14. The pressure above the solutions in cells 12 and 14, therefore, will be the pressure that exists in chamber 70.

Pressure chamber 70 communicates through two-position control valve 78 with two different pressure sources, first pressure source 74 and second pressure source 76. When valve 78 is in a first position, chamber 70 is exposed to first pressure source 74, and the pressure in chamber 70 is $P_1$. When valve 78 is in its second position, chamber 70 is exposed to second pressure source 76, and the pressure in chamber 70 is $P_2$. Moving valve 78 from its first to its second position, therefore, causes the solutions in cells 12 and 14 to experience a pressure perturbation of, e.g., $+\Delta P$. Similarly, moving valve 78 from its second to its first position causes the solutions to experience a pressure perturbation of, e.g., $-\Delta P$.

In one embodiment, first pressure source 74 is the atmosphere, and second pressure source 76 is a variable pressure air tank. $P_1$, therefore, is about 1 atm, and $P_2$ is selected manually by the user in advance of a scan. Alternatively, both pressure sources can be variable, and both can be controlled by computer 20, allowing a user to change the pressure differential $\alpha P$ during a scan. Other types of pressure sources, such as pneumatic pumps and variable pressure chambers, can also be used.

Valve 78 can be any type of appropriate two-position control valve known in the art. In one embodiment valve 78 includes a sliding closure member that blocks either connection 80 to first pressure source 74, or connection 82 to second pressure source 76, but not both. Alternatively, valve 78 can be an electrically operated stopcock device.

Valve 78 is controlled by computer 20. At specified points during a scan, computer 20 causes valve 78 to switch its current position, e.g., by operating a motor that moves a sliding closure member. In one embodiment, pressure sensor 72 is a commercially available sensor manufactured by Cole-Parmer Instrument Co., Vernon Hills, Ill., Part No. P-68023-13. The Cole-Parmer sensor continuously monitors the pressure in chamber 70 and relays the pressure data to computer 20.

Automated Operation of the Pressure Perturbation Calorimeter

Figure 2:
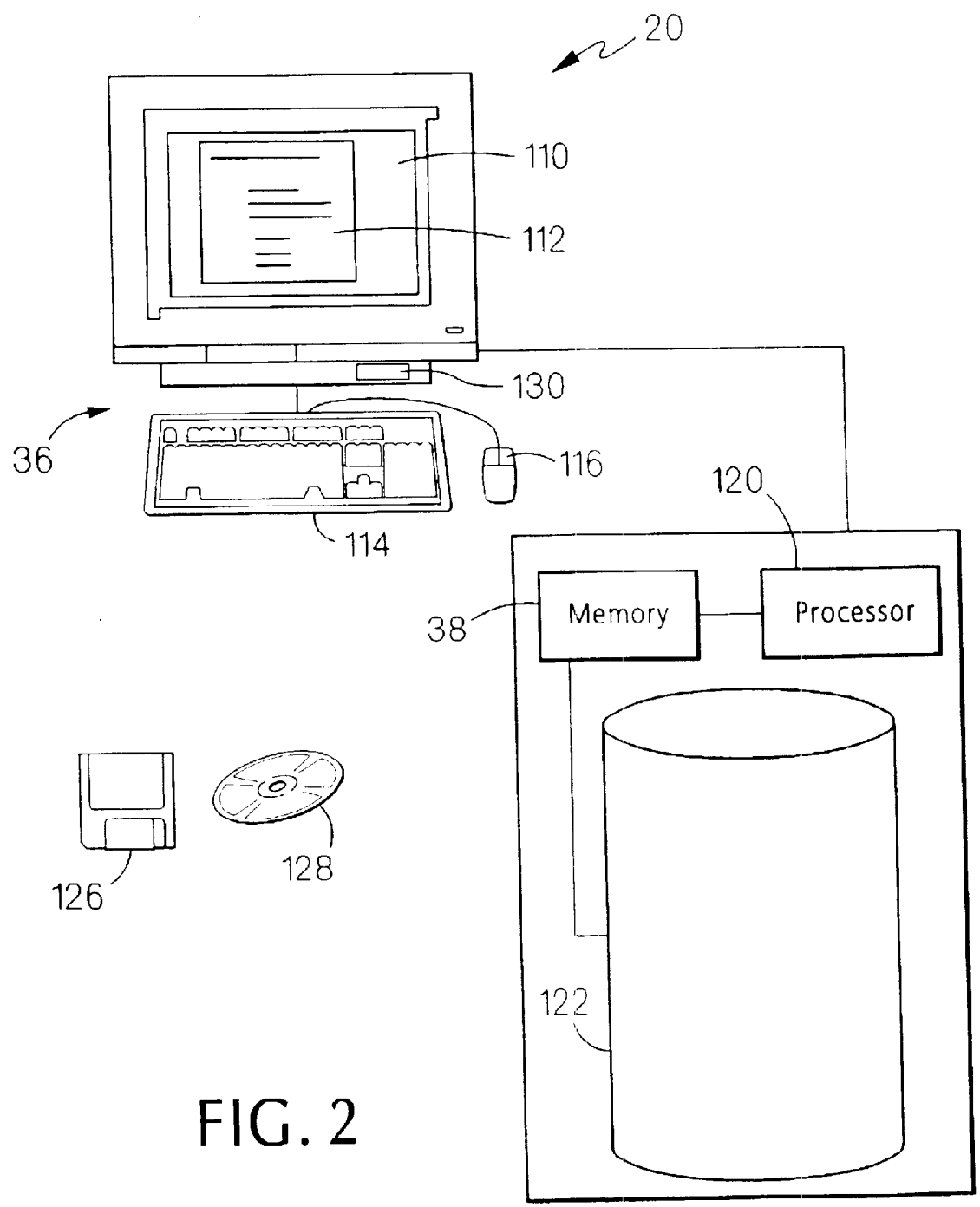
FIG. 2 is a schematic diagram of a computer portion of the calorimeter of FIG. 1.

Operation of calorimeter 10 is automated by computer 20 and associated computer software. Referring to FIG. 2, interface 36 of computer 20 includes a monitor 110 for displaying information 112 to a user, and an input mechanism, such as a keyboard 114 or a mouse 116. Computer 20 also includes a processor 120, an internal storage medium 122, e.g., a hard drive, and random access memory 38.

Software for operating calorimeter 10 is stored on a program storage device readable by computer 20. For example, the software can be stored on internal storage medium 122, or on a magnetic disk 126, an optical disk 128, a magnetic tape, or other storage medium readable by a drive 130 in computer 20.

To operate calorimeter 10 in scanning mode, a user and the software perform the following steps. First, the user fills reference cell 12 and tube 16 completely with a solution, e.g., a saline solution, and fills cell 14 and tube 18 completely with a test substance dissolved in the same solution. The test substance can be, e.g., a protein. Typically, the dissolved test substance will be at a concentration of only about 1% in cell 14.

Next, using input mechanism 116 of interface 36, the user enters the desired scan rate, the desired temperature range for the scan, the desired filter time, the desired pressures $P_1$ and $P_2$ for pressure sources 74 and 76 respectively, and the desired temperatures where pressure perturbations are to be applied. A typical scan rate can be, e.g., about 6° C. per hour, but can be faster or slower. Pressure perturbations can be set to occur, e.g., every 3° C., or every 30 minutes. The user can also instruct heating assembly 22 to operate in adiabatic mode, improved adiabatic mode, or non-adiabatic mode, and to use either active or passive compensation, as described above.

After the user has finished entering the experimental parameters, the user instructs the system to begin heating (or cooling) the cells at the selected scan rate. At the beginning of the scan, the pressure in chamber 70 will be equilibrated to, e.g., pressure $P_1$. After 3° C. of scanning, computer 20 switches valve 78 to its other position, thereby changing the pressure in chamber 70 from $P_1$ to $P_2$, which in turn changes the pressure above the solutions in cells 12 and 14. If $P_2$ is larger than $P_1$, then switching valve 78 will typically cause the solutions in the cells to release heat. Using sensor 42, thermal effect measuring device 40 continuously monitors any resulting temperature differential between cells 12 and 14, and reports these data to computer 20. Simultaneously, absolute temperature measuring device 46 uses sensor 48 to detect the temperature of shield 44, and continuously reports the temperature to computer 20. Computer 20 filters the data from devices 40 and 46, and stores the data as discrete data points in memory 38, one measurement per filter time interval.

Once the cells have equilibrated to pressure $P_2$, typically several minutes after valve 78 switches to second pressure source 76, computer 20 commands valve 78 to switch the pressure in chamber 70 back to $P_1$. If $P_1$ is less than $P_2$, then the change back to $P_1$ causes the solutions in cells 12 and 14 to absorb heat. As before, device 40 continuously reports any resulting temperature differential as the pressure in the cells equilibrates, and device 46 continuously reports the temperature of shield 44. Once the pressure in chamber 70 re-equilibrates to $P_1$, the pressure is maintained at $P_1$ until the next designated time or temperature for pressure perturbations.

Calorimeter 10 continues the same pressure perturbation pattern, e.g., a pair of perturbations every half-hour, until the full temperature scan has been completed. Throughout the scan—both during and between pressure perturbations—device 40 continuously reports temperature differential data to computer 20. Computer 20 continuously filters and stores the data in memory 38 as discrete data points, one measurement per filter time interval.

At the conclusion of the scan (or, alternatively, during the scan), the software gathers the temperature differential data and generates a graph depicting differential heat capacity, $\Delta C_p$, (calories/degree) versus temperature over the temperature range of the scan. The graph allows a user to determine the heat absorbed or released by the substance in response to a pressure perturbation (the "pressure induced heat effect").

To generate the graph, the software first converts the temperature differential data points recorded during the scan into power differentials using the equation:

$$\text{Power differential} = c\Delta T$$

where $\Delta T$ is the temperature differential for a particular filter time interval, and c is a proportionality constant. The proportionality constant c varies depending on the feedback gain setting (active versus passive compensation) of calorimeter 10. The different proportionality constants for different feedback gain settings are stored in the software.

The software next converts the power differentials to differential heat capacities, $\Delta C_p$, by dividing the power differentials by the scan rate (degrees/minute). The software then constructs a graph showing $\Delta C_p$, plotted versus temperature for the length of the scan. Alternatively, the user can instruct the software through interface 36 to display the data as differential power versus time, or in another form.

The graph of $\Delta C_p$, versus temperature contains exothermic and endothermic peaks for each pair of pressure perturbations. The area under each compression or decompression peak ($\Delta C_p$ integrated over a temperature interval, or differential power integrated over time) gives the pressure induced heat effect (i.e., the heat $\Delta Q$ absorbed or released by the test substance in response to the pressure perturbation). The graph, as well as the raw data, are reported to the user via monitor 110 of computer 20. A sample graph is described below with reference to FIG. 4.

Calorimeter 10 can also be operated in an "isothermal mode" rather than in scanning mode. In isothermal mode, after obtaining pressure-induced compression and decompression peaks at a temperature $T_1$, the heating assembly 22 quickly changes the temperatures of the cells to temperature $T_2$ and repeats the pressure perturbations at that temperature. After the data is collected for the pressure perturbations at $T_2$, the instrument repeats these steps for a sequence of additional temperatures until all the pre-selected temperatures have been included. At each temperature $T_n$, heating assembly 22 holds the temperature constant (i.e., "isothermal") during the pressure perturbations. The resulting data will generally be displayed as power differentials versus time.

In isothermal mode, the instrument baseline is more constant and exhibits less noise, thereby providing higher sensitivity. Unlike in scanning mode, however, in isothermal mode, the user does not obtain data for heat released or absorbed at the default pressure, e.g., $P_1$, for temperatures between each $T_n$.

From the collected data, the software calculates certain information about the test substance. For example, in the embodiment described below, the software determines thermal coefficients of expansion of the partial molar volume, $\alpha$, for the dissolved substance, and the precise change in volume, $\Delta V$, of the substance as it undergoes transition from one three-dimensional structure to another.

Using the Pressure Perturbation Calorimeter to Determine $\alpha$ and $\Delta V$ of a Test Substance In one embodiment, the software program in calorimeter 10 determines the thermal coefficient of expansion, $\alpha$, of a protein, both before and after the protein unfolds. In addition, the software program precisely determines the change in volume, $\Delta V_{unf}$, of the protein as it unfolds.

Unfolding of Proteins and Protein Stability

Proteins exist in nature in a "folded," three-dimensional conformation. If a protein is heated to a temperature higher than its denaturing point, however, the protein loses its natural three-dimensional structure and "unfolds." As it unfolds, the volume of the protein changes, since hydrophobic sidechains ordinarily buried within the native protein are exposed to the exterior, and become solvated.

The volume change for unfolding a protein has long been recognized as an important structural parameter. Some researchers also have recently demonstrated a strong correlation between the thermal expansion of native protein surface and the stability of the protein to unfolding. See Palmer and Curmi, *Protein Science*, 8:913–20 (1999). Palmer and Curmi's findings suggest that native proteins folded in a highly-stable manner are "rock-like," and therefore resistant to expansion as the temperature is increased. Proteins folded in a less-stable manner, however, have more looseness of structure and, consequently, expand more readily with increasing temperature. In view of their findings, Palma and Curmi feel that thermal expansion could be a parameter that can help to both understand and predict protein stability. Thermal expansion data, therefore will be useful for bioengineering and other applications.

Derivation of a Relationship Between $\Delta Q$, $\Delta P$ and $\alpha$

To calculate the thermal coefficient of expansion, $\alpha$, of a protein molecule from pressure perturbation calorimetry data, it is first necessary to derive an equation relating $\alpha$ to the heat effect, $\Delta Q$, and the pressure perturbation, $\Delta P$. In this section, a relationship between $\alpha$, $\Delta Q$, and $\Delta P$ is derived for liquids. In the next section, the derived relationship is modified to allow calculation of $\alpha$ values for solutes in a dilute solution.

An equation relating $\alpha$, $\Delta Q$, and $\Delta P$ for liquids can be derived directly from the second law of thermodynamics. From the second law, the definition of entropy can be stated as:

$$dS = \frac{dQ_{rev}}{T} \tag{1}$$

where dS is the entropy change for a reversible process carried out at temperature T whose heat change is $dQ_{rev}$. Differentiating Eq. 1 with respect to pressure, P, at constant T, and rearranging, gives:

$$\left(\frac{\partial Q_{rev}}{\partial P}\right)_T = T\left(\frac{\partial S}{\partial P}\right)_T \tag{2}$$

Using the well-known Maxwell Relation:

$$\left(\frac{\partial S}{\partial P}\right)_T = -\left(\frac{\partial V}{\partial T}\right)_P \tag{3}$$

and substituting into Eq. 2 gives:

$$\left(\frac{\partial Q_{rev}}{\partial P}\right)_T = -T\left(\frac{\partial V}{\partial T}\right)_P = -TV\alpha \tag{4}$$

where V is the volume and $\alpha$ is the coefficient of thermal expansion:

$$\alpha = \frac{1}{V}\left(\frac{\partial V}{\partial T}\right)_P.$$

Integration of Eq. 4 at constant temperature and over a short pressure range gives the equation:

$$\Delta Q_{rev} = -TV\alpha\Delta P \tag{5}$$

In this final integration, it is assumed that V and $\alpha$ are nearly invariant with small pressure changes, which is a very good approximation for all liquids.

The accuracy of Eq. 5 was verified by performing the following experiment using calorimeter 10. Identical samples of pure water (0.506 ml) were inserted into both sample cell 14 and reference cell 12. An excess nitrogen pressure of 9.0 psi was applied above water in sample cell 14, while maintaining atmospheric pressure on reference cell 12. (For this experiment, calorimeter 10 was modified so that pressure chamber 70 connected only to sample cell 14, leaving reference cell 12 exposed to atmospheric pressure.) The heat evolved as a result of the applied pressure to the sample cell was measured. The excess pressure was then released, and it was observed (as expected) that an identical amount of heat was absorbed when the pressure was released. Measurement of the heat resulting from increase and subsequent release of the same pressure of 9.0 psi was carried out at a series of temperatures from 0 to 70° C.

Figure 3A:
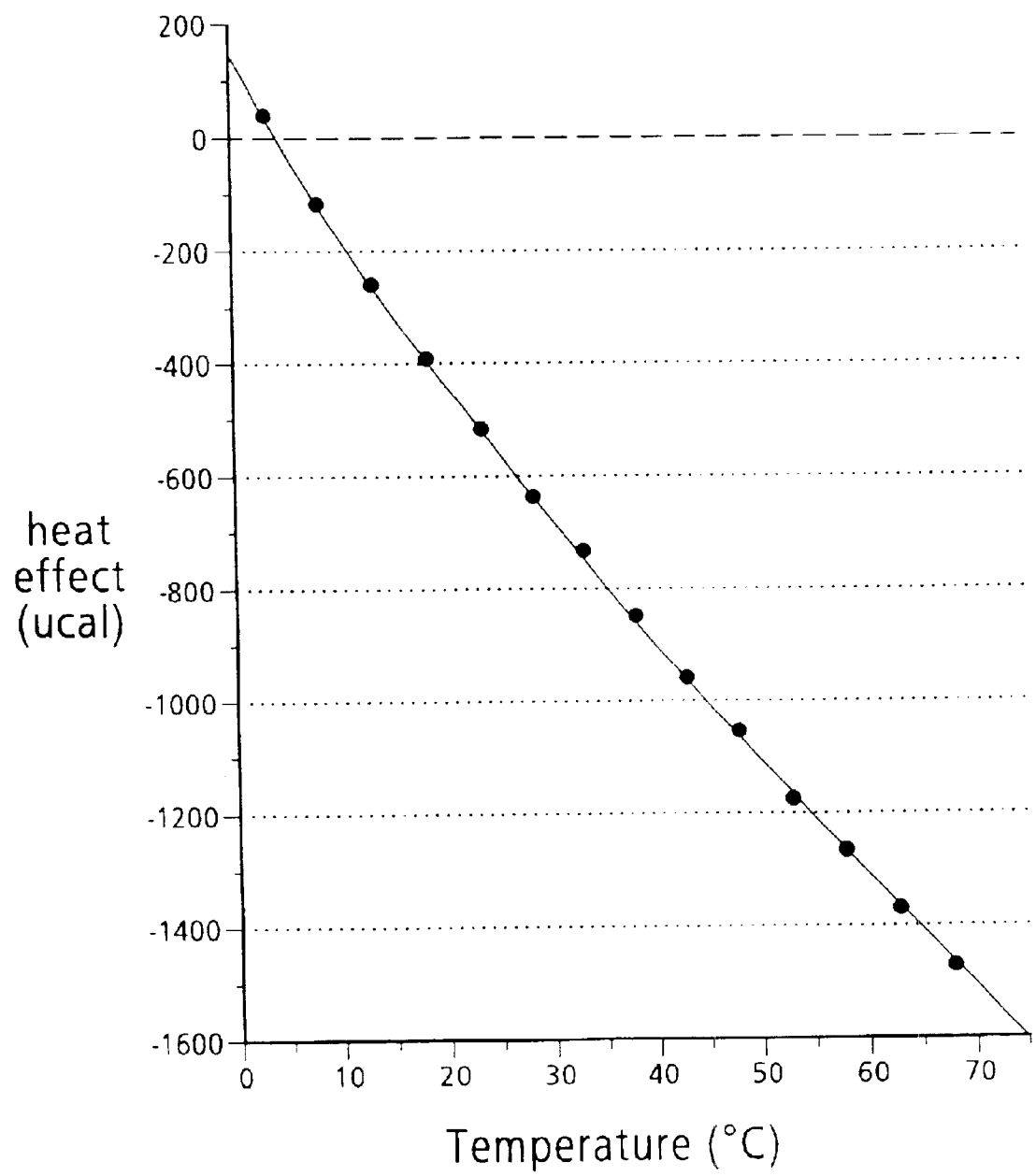
FIG. 3A is a graph demonstrating the accuracy of an equation derived from the second law of thermodynamics.

Experimental data are shown as the data points in the graph of FIG. 3A. The solid line in FIG. 3A represents the heats calculated from the expression:

$$\Delta Q = -TV\alpha_w \Delta P \qquad (6)$$

where $\alpha_w$ is the thermal coefficient of expansion for pure water, calculated from accurate density data provided in Kell, J. Chem. Engineering Data, 12:66–72 (1967). Note that the heat effect, $\Delta Q$, reverses sign at 4° C., since at this temperature $\alpha_w$ changes sign, reflecting the maximum in the density of water at that temperature.

As is clear from visual inspection of FIG. 3A, the experimental data agree well with the results predicted by the Eq. 5.

Application of Eq. 5 to Solutions to Determine α for Dissolved Solutes

To determine the thermal coefficient of expansion of a solute in a dilute solution from pressure perturbation calorimetry data, Eq. 5 must be modified to account for displacement of solvent by solute molecules. The derivation below yields an equation that allows direct calculation of α values for a dissolved solute.

When a solution is formed by dissolving $g_1$ grams of a solute in $g_0$ grams of a solvent, then the total volume, $V_{total}$, of the resulting solution may be expressed as:

$$V_{total} = g_0 V_0 + g_1 V_1 \qquad (7)$$

where $V_0$ is the specific volume of pure solvent, and $V_1$ is defined as the apparent partial specific volume of the solute in the solution. The partial specific volume of many solutes, including biopolymers, have been reported in the literature for near room temperature.

If the above equation is differentiated with respect to temperature, this leads to:

$$\left(\frac{\partial V_{total}}{\partial T}\right)_P = g_0 \left(\frac{\partial V_0}{\partial T}\right)_P + g_1 \left(\frac{\partial V_1}{\partial T}\right)_P \qquad (8)$$

Substituting the right hand side of Eq. 8 into Eq. 4 of the previous section, we obtain:

$$\left(\frac{\partial Q_{rev}}{\partial P}\right)_T = -T\left[g_0 \left(\frac{\partial V_0}{\partial T}\right)_P + g_1 \left(\frac{\partial V_1}{\partial T}\right)_P\right] \qquad (9)$$

Multiplying and dividing the first term in brackets by $V_0$ and multiplying and dividing the second term in brackets by $V_1$ gives:

$$\left(\frac{\partial Q_{rev}}{\partial P}\right)_T = -T[g_0 V_0 \alpha_0 + g_1 V_1 \alpha_1] \qquad (10)$$

where $\alpha_0$ is the thermal coefficient of expansion for the solvent, and $\alpha_1$ is the thermal coefficient of expansion of the solute. According to Eq. 10, the heat arising from pressure perturbation of a dilute solution can be viewed as the sum of that arising from the perturbation of the solvent in the solution and from the perturbation of the solute in the solution. The contribution from the solvent is weighted by the coefficient of expansion of pure solvent, $\alpha_0$, times the apparent total volume ($g_0 V_0$) occupied by the solvent, and the contribution from the solute is weighted by the coefficient of expansion of the solute, $\alpha_1$, times the apparent total volume ($g_1 V_1$) occupied by the solute in the solution.

Finally, Eq. 10 can be integrated over a short pressure range to obtain:

$$\Delta Q_{rev} = -T[g_0 V_0 \alpha_0 + g_1 V_1 \alpha_1] \Delta P \qquad (11)$$

Figure 3B:
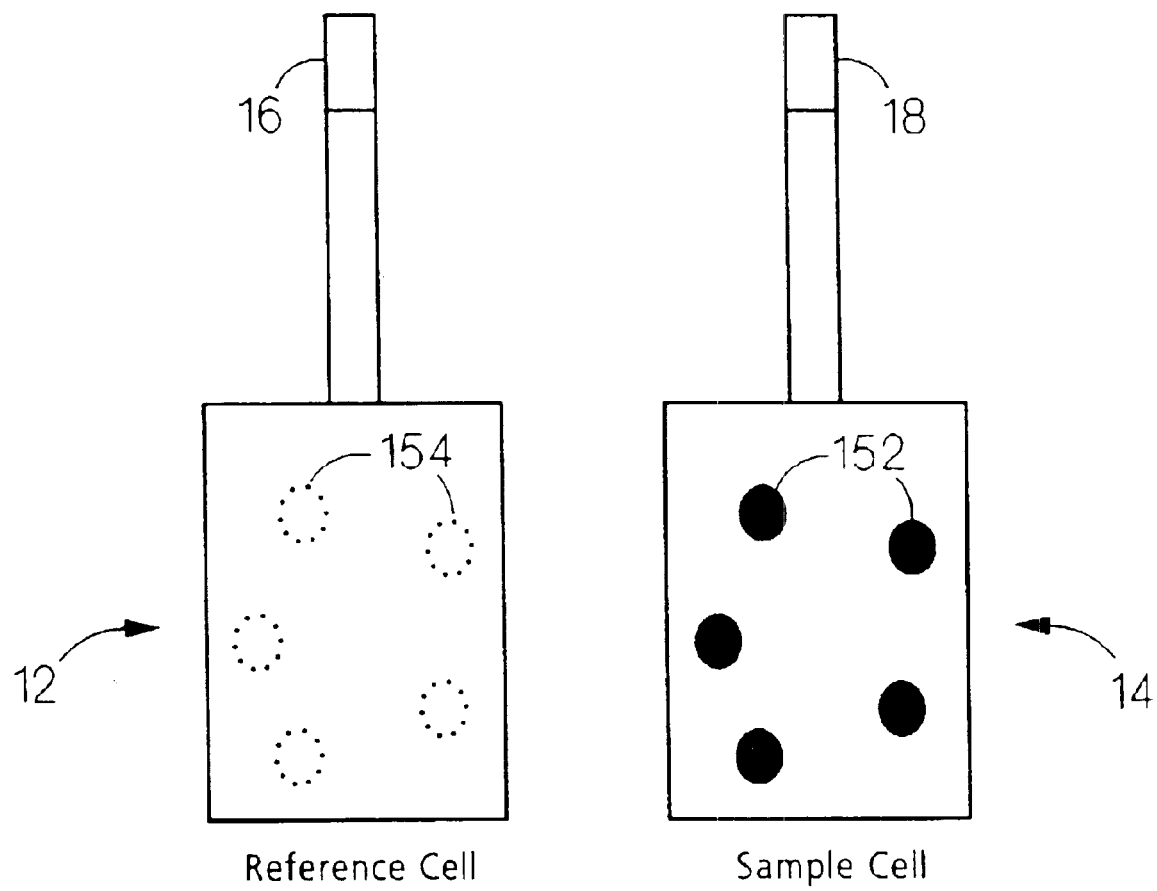
FIG. 3B is a schematic diagram illustrating solvent volumes in the sample and reference cells of the calorimeter of FIG. 1.

When carrying out a pressure perturbation experiment, the sample cell is filled with the solution containing the solute and the reference cell is filled with the pure solvent. In the case of a biopolymer solution, the "pure solvent" will normally be the identical buffer in which the biopolymer is dissolved. This situation is depicted in FIG. 3B, where the solute molecules 152 are indicated as dark objects in sample cell 14. Assuming that sample cell 14 and reference cell 12 have exactly identical total volumes $V_{cell}$, then the reference cell will contain more solvent than the sample cell, since in the sample cell, some of the solvent is displaced by the solute molecules 152. The volume of "displaced solvent" in the sample cell will be equal to $g_1'V_1 V_{cell}$, where $g'_1$ is the concentration of solute in g/ml (i.e., $g_1 = g_1' V_{cell}$). The extra solvent volume in the reference cell is that enclosed by dashed lines 154, corresponding to solute molecules 152 in the sample cell. If a pressure perturbation is then carried out by simultaneously pressuring both cells by $\Delta P$, the heat observed, $\Delta Q_{rev}$, will be equal to that produced in sample cell 14 less that produced in reference cell 12. That is, the resultant heat will be equal to that produced by thermal expansion of solute molecules in the sample cell minus that produced by an equivalent volume of pure solvent in the reference cell:

$$\Delta Q_{rev} = -T[g_1' V_{cell} V_1 \alpha_1 - g_1' V_{cell} V_1 \alpha_0] \Delta P \qquad (12)$$

The coefficient of expansion of the solute $\alpha_1$ is then equal to:

$$\alpha_1 = \alpha_0 - \frac{\Delta Q_{rev}}{T \Delta P g_1' V_1 V_{Cell}} \qquad (13)$$

All quantities in the second term on the right of Eq. 13 are known either from experiment ($\Delta Q_{rev}$, T, $\Delta P$, $V_{cell}$, and $g'_1$) or from the literature. ($V_1$ literature values at a single temperature are usually available. Since $\alpha_1$ values are usually about $10^{-4}$ deg$^{-1}$, neglect of the temperature dependence of $V_1$ in the denominator of the second term in Eq. 13 does not affect the calculated $\alpha_1$ value appreciably.)

Obtaining an accurate value for $\alpha_1$ from Eq. 13 requires knowing the value of $\alpha_0$ as a function of temperature. If the solvent is aqueous buffer containing low concentration of salts, then it is usually sufficient to use the literature values of a for pure water. If the buffer contains high concentrations of electrolytes and other additives, then $\alpha_0$ must be measured experimentally. This can be readily done in a second pressure perturbation experiment with the buffer of interest in the sample cell and pure water in the reference cell, using α values from the literature for pure water.

Calculation of α and $\Delta V_{unf}$ of a Protein from Pressure Perturbation Calorimeter Data FIG. 4 is a graph depicting data output for operation of calorimeter 10. These representative data were gathered using the protein chymotrypsinogen as the test substance. Calorimeter 10 was set in adiabatic scanning mode with active compensation and a filter rate of about five seconds. Pressure perturbation pairs of +2.3 atm and −2.3 atm were applied every 3 minutes. The scan rate was 6°/hour, and the chymotrypsinogen concentration in sample cell 12 was 2% by weight. The buffer was an HCl-water solution with a pH of 2.3.

The graph shows $\Delta C_p$ on the vertical axis, and temperature on the horizontal axis. The data show a number of pairs of pressure perturbation peaks 208 over a portion of a temperature scan stretching from 20° C. to 70° C. Box 210 provides an enlarged view of a single pair of pressure peaks. The large peak 212 between T=32° C. and T=61° C. is the temperature range over which the protein unfolded. From this data, chymotrypsinogen appears to have a major unfolding transition centered at about 47° C.

The thermal coefficients, $\alpha$, for both the native protein ($\alpha_{nat}$) and the unfolded protein ($\alpha_{unf}$), as well as the $\Delta V_{unf}$ are calculated in the following manner. First, the heat effect $\Delta Q$ for each pressure peak 208 in the graph of FIG. 4 is obtained by determining the area of each peak above or below a baseline 211 (see box 210). The area for each decompression peak (designated $-\Delta P$ in box 210) will be equal in magnitude and opposite in sign to the corresponding compression peak. The resulting data set ($\Delta Q$ values as a function of temperature) is then used along with other known quantities ($V_1$, $V_{cell}$, $\Delta P$, T, and $g_1$) to obtain values for the thermal coefficient of the protein, $\alpha_1$, by applying Eq. 13.

For this particular experiment, the "buffer" was pure water (with HCl added to bring the pH to 2.3). Since the buffer did not contain high concentrations of electrolytes, the thermal coefficient of the solvent, $\alpha_0$, was virtually identical to the thermal coefficient of pure water, $\alpha_w$, a value well established in literature.

Figure 5:
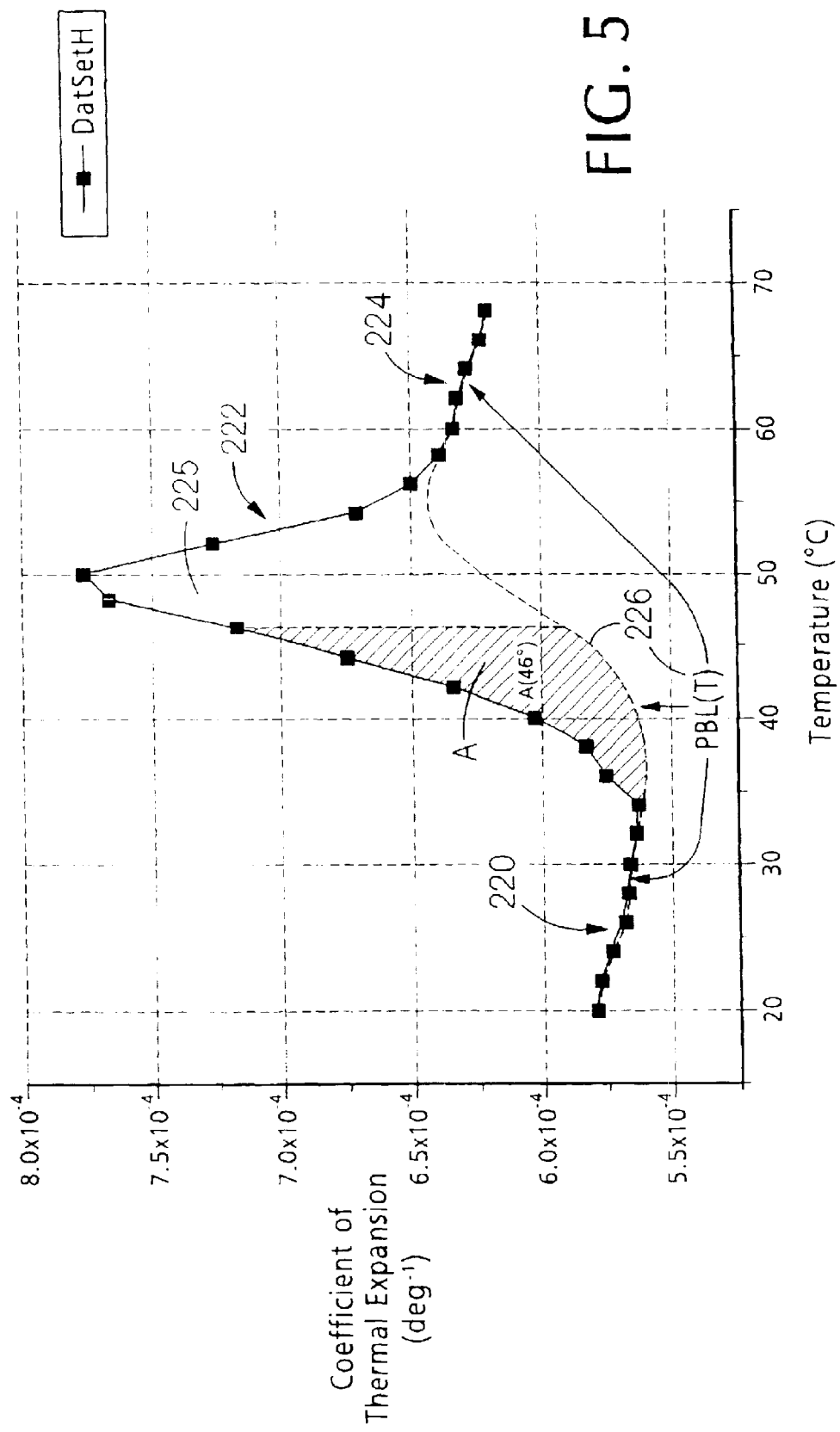
FIG. 5 is a graph of the thermal coefficient of expansion versus temperature derived from the data of the graph of FIG. 4.

The $\alpha_1(T)$ values obtained in this particular experiment are shown in the graph of FIG. 5. The function $\alpha(T)$ of FIG. 5 has three distinct regions: (1) A first straight line region 220 between T=20° and T=32° corresponding to the native protein; (2) a middle transition region 222 between T=32° C. and T=61° C. corresponding to the temperature range in which the protein is unfolding; (3) and a second straight line region 224 between T=61° and T=68° corresponding to the unfolded protein.

Thermal coefficients of expansion for the protein chymotrypsinogen in both its native and unfolded states are readily obtainable from the data of FIG. 5. For example, the thermal coefficient of expansion for the native protein, $\alpha_{nat}(T)$, decreases slightly with temperature, and has a value of $5.75 \times 10^{-4}$ deg$^{-1}$ at 30° C. The $\alpha$ function for the unfolded protein, $\alpha_{unf}(T)$, also decreases with temperature, and has a value of $6.35 \times 10^{-4}$ deg$^{-1}$ at 60° C.

The volume change $\Delta V_{unf}$ for the protein is calculated by determining the area of peak 225 in the transition region, and then multiplying the area by the known molar volume of the protein. The area of peak 225 correlates to the volume change, because the transition region 222 would be a smooth curve connecting straight line regions 220 and 224, rather than a peak, if the protein did not change volume as it unfolded. In this embodiment, the area of peak 225 is calculated by measuring the area between a spline function computed to connect straight line regions 220, 224, and a function defined by the data of transition region 222.

First, the software defines an $\alpha_{nat}(T)$ function for region 220 by fitting a straight line through the data points in region 220. The software then defines an $\alpha_{unf}(T)$ function in the same manner for region 224. Once these two linear baselines are defined, the two straight line segments are automatically connected by the software with a spline function to give a "trial" progress baseline 226. The progress baseline 226 should generally obey the equation:

$$PBL(T)=f_{Nat}(T)\alpha_{Nat}(T)+f_{Unf}(T)\alpha_{Unf}(T)=[1-f_{Unf}(T)]\alpha_{Nat}(T)+f_{Unf}(T)\alpha_{Unf}(T) \quad (14)$$

where $f_{Nat}(T)$ is the fraction of the protein in its native state and $f_{Unf}(T)$ is the fraction of the protein in its unfolded state, and all functions are evaluated at the same temperature T. As evident from Eq. 14, the progress baseline is the experimental curve one would hypothetically obtain if there were no change in volume for the transition of native state to unfolded state. In other words, the spline region 226 is a function $\alpha(T)$ for a protein composition that is a mixture of native and unfolded proteins, assuming no $\Delta V_{unf}$. Note that the progress baseline of Eq. 14 is also accurate for regions 220 and 224, where only the native or unfolded protein exists.

The trial progress baseline is then improved using an iteration process. Using the trial baseline, partial areas are calculated between progress baseline 226 and the data points in the transition region. One such partial area is area A in FIG. 4. It is assumed that the fraction of the unfolded state is equal to the partial area up to a temperature T divided by the total area up to the final temperature in the scan:

$$f_{Unf}(T)=A(T)/A_{tot} \quad (15)$$

Solving Eq. 15 at each temperature where a data point exists gives a data set for $f_{Unf}(T)$. These values are then plugged back into Eq. 14 to generate a new PBL(T) which is improved over the initial PBL(T). This iteration process is continued until successive PBL(T)'s no longer differ significantly from one another.

The total area between the final progress baseline and the experimental data points, $A_{tot}$, is then used to estimate the volume change $\Delta V_{unf}$ for unfolding the protein by applying the relationship:

$$A_{tot} = \int \frac{1}{V}\left(\frac{dV}{dT}\right)dT \cong \frac{1}{V}\int \left(\frac{dV}{dT}\right)dT = \frac{\Delta V_{unf}}{V} \quad (16)$$

$\Delta V_{unf}$ is then obtained by multiplying $A_{tot}$ by the known molar volume or the specific volume V of the protein. V can be pulled outside the integral sign since it is approximately constant ($\Delta V_{unf}$ values for proteins are typically less than 1%). For chymotrypsinogen, $\Delta V_{unf}$ was found to be about 34 ml per mole of protein. Since chymotrypsinogen has a molecular weight of about 25,000 daltons, $\Delta V_{unf}$ corresponds to a volume change of about 0.2%.

In the embodiment described above, the calculation process is fully integrated into the software, such that the software presents to the user at the conclusion of the experiment the final calculations for $\alpha_{nat}(T)$, $\alpha_{unf}(T)$, and $\Delta V_{unf}$. Alternatively, the user can manually calculate some or all of the steps in the above calculation process.

Comparison to Existing Technologies for Calculating $\Delta V_{unf}$ and $\alpha$ Values Some existing methods for calculating the volume change for unfolding a protein use high pressure optical cells to examine changes in optical properties of the materials, e.g., absorbance, fluorescence, or optical rotation. These methods are not particularly accurate, since they require crude and likely incorrect assumptions about the steps in a protein's transition.

A procedure for calculating $\Delta V_{unf}$ using optical cells involves measuring the optical property as a function of pressure at constant temperature, and then carrying out these measurements at a series of different temperatures that span the transition region. Data analysis is based on the fact that the native ($\epsilon_{nat}$) and unfolded protein ($\epsilon_{unf}$) exhibit a different value for the optical property.

The optical studies provide no direct information on volumetric properties of the protein. Thus, to calculate $\Delta V_{unf}$ from optical data, it must be assumed that the transition is accurately represented as a two-state equilibrium including only native proteins and unfolded proteins, and that there are negligible concentrations of states of intermediate folding that occur in the transition region. Making this assumption, a two-state equilibrium constant, K, can be expressed as:

$$K = \frac{[\text{Unfolded}]}{[\text{Native}]} = \frac{\varepsilon - \varepsilon_{Nat}}{\varepsilon_{Unf} - \varepsilon} \quad (17)$$

where $\varepsilon$ is the value of the optical property. The volume change for the transition, $\Delta V_{unf}$, can be estimated from K using the thermodynamic relationships:

$$\Delta G^0 = -RT \ln K \quad (18)$$

and $$\left(\frac{\partial \Delta G^0}{\partial P}\right)_T = \Delta V_{Unf} \quad (19)$$

where $\Delta G^0$ is Gibbs free energy change. The calculations using optical cells provide no information regarding the thermal coefficients of expansion, $\alpha$, for the native and unfolded states.

Because of the typically small $\Delta V_{unf}$ for proteins, obtaining a measurable shift in K requires use of very high pressures. Accordingly, optical studies are customarily carried out to pressures near or above 5000 atm. To withstand these high pressures, the optical cells must be very heavy-walled steel with expensive sapphire windows and pressurized with a powerful pump utilizing an oil-water interface. By contrast, the new pressure perturbation instruments and methods described herein calculate the volume change directly using only moderate pressures, and do not require any assumptions about the nature of the transition.

In addition, this new methodology allows for easy determination of the thermal coefficient of expansion, $\alpha$, of solutes dissolved in dilute solution. With existing technology, a must be determined either by densitometry or dilatometry. While it is fairly easy to determine $\alpha$ values of pure liquids by these existing methods, their accuracy is seriously challenged when trying to estimate a values for dissolved solutes present at low concentration in solution. The accuracy of pressure perturbation calorimetry is extremely high, so it becomes possible not only to accurately estimate $\alpha$ but also to determine the first and second temperature derivatives of $\alpha$, as indicated in FIG. 5. While this detailed information is of interest for all large and small solutes, it becomes particularly important for biopolymers such as proteins. It has been shown recently (Palmer and Curmi, supra) by computational methods that the stability of native proteins is strongly correlated with the magnitude of $\alpha$. The ready availability of accurate information from experimental studies should facilitate a better understanding of this parameter and how it relates to stability and three-dimensional structure.

Other Embodiments

Other embodiments of the invention are within the scope of the claims. For example, rather than controlling the pressure applied to cells 12 and 14 using a single chamber 70, cells 12 and 14 can communicate with two separate pressure sources. Using separate pressure chambers and pressure sources for the two cells would allow the pressures experienced by the liquids in the two cells to be controlled independently.

Rather than using a two-way valve connecting a pressure chamber to two separate pressure sources, a single, variable pressure source could be placed in direct communication with the cells. The pressure applied above the liquid in the cells could be varied by simply changing the setting of the variable pressure source.

The pressure assembly could be controlled manually, rather than by using automation software.

Rather than directly storing temperature differential data, computer 20 could store in memory 38 differences between the power applied to the sample and reference cells in order to maintain the sample and reference cells at an equal temperature. In other words, computer 20 could store in memory 38 the power differentials required to compensate for any temperature differentials that arise during a scan or during a pressure perturbation.

The heating assembly need not include the various features and temperature control modes described above. The pressure perturbation assembly could be adapted to work with any calorimeter that includes twin cells and a mechanism for measuring differential heat effects, $\Delta Q$, between the two cells.

Other Applications for Pressure Perturbation Calorimetry Data

The pressure perturbation calorimetry instruments and calculation methods described above can be used to determine $\alpha$ and $\Delta V$ for molecules other than proteins. For example, $\Delta V$ can be determined for other molecules that undergo a structural transition driven by temperature, such as DNA and RNA, or certain lipid vesicles, carbohydrates, or synthetic polymers. Thermal coefficients $\alpha$ can be calculated for essentially any organic or inorganic substance, including any solute in an aqueous or non-aqueous solvent.

In addition, pressure perturbation calorimetry data can be used to determine solvation parameters for proteins and other molecules.

The test substance in the sample cell need not be in the form of a dilute solution. For example, concentrated solutions of a test substance could be compared directly to pure solvent to determine, e.g., thermodynamic properties of the test substance.

A pressure perturbation assembly could also be used in conjunction with an isothermal titration calorimeter or other mixing calorimeters. As discussed above, in isothermal titration calorimetry, the concentration of a ligand that binds to the test substance is varied while the temperature is held constant. Binding of a ligand to any other target molecule, e.g., a biopolymer such as a protein or an oligonucleotide, results in changes in the coefficient of thermal expansion of the biopolymer as well as changes to the volume occupied by the biopolymer. To determine information about $\alpha$ and $\Delta V$ using a pressure perturbation titration calorimeter, experiments could be performed in which the reference cell would contain a solvent and a binding ligand at a fixed concentration. The sample cell would contain the solvent, target molecule (at a fixed concentration) and the binding ligand at the same initial concentration as the reference cell. The concentration of the binding ligand in the sample cell and the reference cell would then be varied, and pressure perturbations would be applied to the two cells at each concentration. The output data would be $\Delta Q$ versus ligand concentration, allowing calculation of a for the target molecule and the $\Delta V$ that results from binding of the ligand. If desirable, these experiments could also be carried out at different temperatures for each ligand concentration, or for selected ligand concentrations.

In addition, the effects from other solution variables, such as pH, ionic strength, and addition of co-solvents, could be studied.

What is claimed is:

1. A computer-readable medium for use with a calorimeter including a digital processor system, a first liquid holder containing a solution containing a plurality of target molecules, and a second liquid holder containing a liquid in which no target molecules are present, said computer-readable medium storing a program for determining a change in volume occupied by the target molecule as the molecule transitions from a first structure to a second structure in response to a change temperature, wherein said program when executed on the processor system causes the calorimeter to:

(a) at each of a plurality of temperatures that span a range in which the target molecules transition from the first structure to the second structure,
   (i) apply a pressure perturbation to the solution in the first liquid holder and to the liquid in the second liquid holder at that temperature; and
   (ii) record temperature data associated with the pressure perturbation;
   (iii) from the recorded temperature data, determine the value of a specific property of the substance at that temperature, said specific property being a function of the thermal coefficient of expansion of the target molecules, and
(b) from the values of said specific property at the plurality of temperatures, calculate a change in volume occupied by the target molecule.

2. The computer-readable medium of claim 1, wherein the program when executed on the processor system causes the calorimeter to calculate the change in volume occupied by the target molecule by using the pressure perturbation values, the temperatures at which each pressure perturbation was applied, and the volume of an individual target molecule in either its first or its second structure.

3. The computer-readable medium of claim 1, wherein the target molecule is selected from the group consisting of a protein, an oligonucleotide, a lipid, and a carbohydrate.

4. The computer-readable medium of claim 1, wherein said specific property is the thermal coefficient of expansion ($\alpha$) of the substance.

5. The computer-readable medium of claim 1, wherein the program when executed on the processor system causes the calorimeter to determine the value of said specific property of the substance at that temperature by:
   (i) determining a differential heat effect between the first and second liquid holders in response to the pressure perturbation;
   (ii) calculating, from the differential heat effect, the heat effect of the target molecule in response to the pressure perturbation; and
   (iii) determining, from the calculated heat effect at that temperature, the value of the specific property.

6. The computer-readable medium of claim 5, wherein the program when executed on the processor system causes the calorimeter to calculate the change in volume by:
   constructing a function $\alpha(T)$ over a range defined by the plurality of temperatures;
   identifying a transition temperature range during which the target molecule is actively transitioning from the first structure to the second structure; and
   computing an area under $\alpha(T)$ over the transition temperature range.

7. The computer-readable medium of claim 6, wherein the program when executed on the processor system causes the calorimeter to calculate the change in volume by also constructing a baseline function $\alpha_2(T)$ for the transition range and wherein said under $\alpha(T)$ is an area between $\alpha(T)$ and $\alpha_2(T)$ over the transition temperature range.

8. The computer-readable medium of claim 7, wherein $\alpha_2(T)$ represents the thermal expansion coefficient that would have been measured in the transition range if the molecule did not change volume as it transitioned from its first to its second structure.

9. The computer-readable medium of claim 7, wherein the program when executed on the processor system causes the calorimeter to iteratively construct the baseline function $\alpha_2(T)$.

10. The computer-readable medium of claim 7, wherein the program when executed on the processor system causes the calorimeter to construct the baseline function $\alpha_2(T)$ by using a spline function to approximate $\alpha_2(T)$.

11. A calorimeter comprising:
   a sample cell for holding a solution containing a plurality of target molecules;
   a reference cell for holding a liquid in which no target molecules are present;
   a temperature control subsystem that during operation controls a temperature of at least the sample cell;
   a pressure subsystem that during operation applies a selected one of a plurality of different pressures to at least the sample cell;
   a processor subsystem that controls the temperature control subsystem and the pressure subsystem; and
   a memory storing a program which when executed by the processor subsystem causes the calorimeter to:
   (a) at each of a plurality of temperatures that span a range in which the target molecules transition from A first structure to A second structure,
      (i) apply a pressure perturbation to the solution in the sample cell and to the liquid in the reference cell at that temperature; and
      (ii) record temperature data associated with the pressure perturbation;
      (iii) from the recorded temperature data, determine the value of a specific property of the substance at that temperature, said specific property being a function of the thermal coefficient of expansion of the target molecules, and
   (b) from the values of said specific property at the plurality of temperatures, calculate a change in volume occupied by the target molecule.

12. The calorimeter of claim 11 wherein the program when executed on the processor system causes the calorimeter to determine the value of said specific property of the substance at that temperature by:
   (i) determining a differential heat effect between the sample cell and the reference cell in response to the pressure perturbation;
   (ii) calculating, from the differential heat effect, the heat effect of the target molecule in response to the pressure perturbation; and
   (iii) determining, from the calculated heat effect at that temperature, the value of the specific property.

* * * * *